US005753220A

United States Patent [19]

Suzuki et al.

[11] Patent Number: 5,753,220

[45] Date of Patent: May 19, 1998

[54] CYSTEINE PROTEASE GENE DEFECTIVE BACULOVIRUS, PROCESS FOR ITS PRODUCTION, AND PROCESS FOR THE PRODUCTION OF ECONOMIC PROTEIN BY USING THE SAME

[75] Inventors: Takeo Suzuki, Matsumoto; Akihiro Usami, Sayama; Kouhei Oda, Izumi; Hajime Mori, Kyoto; Toshimichi Kanaya, Matsumoto, all of Japan

[73] Assignee: Katakura Industries Co., Ltd., Tokyo, Japan

[21] Appl. No.: 404,445

[22] Filed: Mar. 15, 1995

[30] Foreign Application Priority Data

Mar. 15, 1994 [JP] Japan ................... 6-068961
Jan. 19, 1995 [JP] Japan ................... 7-023296

[51] Int. Cl.$^6$ ................... A61K 48/00; C12N 15/64; C12N 15/86
[52] U.S. Cl. ................... 424/93.2; 435/69.1; 435/69.4; 435/69.51; 435/192.3; 435/320.1
[58] Field of Search ................... 435/69.1, 69.8, 435/172.1, 172.3, 235.1, 320.1, 69.4, 69.3, 69.5, 69.51, 69.52; 424/93.6, 93.2

[56] References Cited

PUBLICATIONS

Winstanley et al., J. Gen. Virol., vol. 74, pp. 1599–1609, 1993.

*Primary Examiner*—David Guzo
*Attorney, Agent, or Firm*—Oblon, Spivak, McClelland, Maier & Neustadt, P.C.

[57] ABSTRACT

For the expression of a foreign gene, a virus is provided in which at least a part of a cysteine protease gene present on a genome of a baculovirus has been deleted or substituted by a marker gene. A process is also disclosed for the formation of the virus. A transfer vector for the deletion of a cysteine protease gene is also described. This transfer vector comprises a DNA fragment of a nuclear polyhedrosis virus genome, in which at least a part of a cysteine protease gene has been substituted by a marker gene, and a plasmid vector fragment. Also disclosed is a process for the production of an economic protein. This production process comprises inoculating a host insect with a gene recombination virus, said gene recombination virus having been obtained by deleting or substituting by a marker gene at least a part of a cysteine protease gene present on a genome of a baculovirus or a nuclear polyhedrosis virus; expressing an economic protein gene inserted downstream a polyhedral gene promoter, granulin gene promoter or p10 gene promoter of the gene recombination virus; and collecting the economic protein.

12 Claims, 9 Drawing Sheets

Map unit

Fragment

Cysteine protease gene

FIG. 3A

```
         10         20         30         40         50         60         70         80         90        100
ATGAACAAAATTTGTTTATTTGTTGTACGCCGTTGTGTAGAGCGGGCCTAGTCAAAGAGCGCCTAATTATTTTGAAGAATTTGTTCATC
 M  N  K  I  L  F  Y  L  F  V  Y  Y  A  V  V  V  K  S  A  A  Y  D  D  P  L  K  A  P  N  Y  F  E  E  F  V  H  R 110        120        130        140        150        160        170        180        190        200
GATTCAACAAAAATTATAGTAGCGAAGTTGAAAAATTGCGAAGATTCAAATTTCCAACACAATTGAAATTATCAATAAAAACGATTC
 F  N  K  N  Y  S  S  E  V  E  K  L  R  R  F  K  I  F  Q  H  N  L  N  E  I  I  N  K  N  Q  N  D  S 210        220        230        240        250        260        270        280        290        300
GGCCAAATATGAAATAAACAAATTCTCGGATTTGTCCAAAGACGAAACTATCGCAAAATACACAGGTCTCTTTGCCTACTCAGACTCAAAATTTTGC
 A  K  Y  E  I  N  K  F  S  D  L  S  K  D  E  T  I  A  K  Y  T  G  L  S  L  P  T  Q  N  F  C 310        320        330    Apal   340        350        360        370        380        390        400
AAGGTCATACTCTTAGACCAGCCGCCCGGGTAAAGGGCCCTTTGAATTTGACTGGCGTCGTCAACAAGTCACTAGCGTAAAAATCAAGGAATGTGTG
 K  V  I  L  D  Q  P  P  G  K  G  P  L  E  F  D  W  R  R  L  N  K  V  T  S  V  K  N  Q  G  M  C  G 410        420        430        440        450        460        470        480        490        500
GCGCCTGCTGGGGTTGCCACTCTGGGCAGTTTGGAAAGTCAATTTGCAATCAAACATAACGATTAATCTGTCGGAGCAGCAAATGATCGATTG
 A  C  W  A  F  A  T  L  G  S  L  E  S  Q  F  A  I  K  H  N  E  L  I  N  L  S  E  Q  Q  M  I  D  C
```

```
         510       520       530       540       550       560       570       580       590       600
TGATTTTGTCGAGGCCGGCTGTAACGGCGGCTTGTTGCATACAGCATTCGAAGCCATCATTAAAATGGGCGGCGTACAGCTGGAAAGCGACTATCCATAC
 D  F  V  D  A  G  C  N  G  G  L  L  H  T  A  F  E  A  I  I  K  M  G  G  V  Q  L  E  S  D  Y  P  Y
                                                       Xcml 610       620       630       640       650       660       670       680       690       700
GAAGCAGAGACAATAACAATTGCCGTATGAACTCTAACAGTTTCTAGTTCAAGTAAAAGATTGTTATAGATACATTATCGTGTACGAGGAAAAACTTAAAG
 E  A  D  N  N  N  C  R  M  N  S  N  K  F  L  V  Q  V  K  D  C  Y  R  Y  I  I  V  Y  E  E  K  L  K  D 710       720       730       740       750       760       770       780       790       800
ATTTGTTACCCCCTTGTCGGCGGGCCCTATTCCTATGGCCCATAGACGCTGCCGACATTGTTAACTATAAACAGGGTATTATAAAATATTGTTTCGACAGCGGTCT
 L  L  P  L  V  G  P  I  P  M  A  I  D  A  A  D  I  V  N  Y  K  Q  G  I  I  K  Y  C  F  D  S  G  L 810       820       830       840       850       860       870       880       890       900
AAACCATGGCGGTTCTTTTAGTGGGTTATGGGTGTTGAAAACAACATTCCGTATTGGACCTTTAAAAACACTTGGGCACGGATTGGGAGGACGGATTT
 N  H  A  V  L  L  V  G  Y  G  V  E  N  N  I  P  Y  W  T  F  K  N  T  W  G  T  D  W  G  E  D  G  F 910       920       930       940       950       960       970
TTCAGGGTACAACAAAACATAAACGCTTGTGTATGGTAGAAAACGAACTTGCCTCTACTGCAGTCATTTATTAA
 F  R  V  Q  Q  N  I  N  A  C  G  M  R  N  E  L  A  S  T  A  V  I  Y  *
```

FIG. 3B

CYSTEINE PROTEASE(−)

P6E (WILD-TYPE VIRUS)

1

CYSTEINE PROTEASE GENE DEFECTIVE BACULOVIRUS, PROCESS FOR ITS PRODUCTION, AND PROCESS FOR THE PRODUCTION OF ECONOMIC PROTEIN BY USING THE SAME

BACKGROUND OF THE INVENTION (i) Field of the Invention

This invention relates to a cysteine protease gene defective baculovirus useful in gene manipulation which makes use of an insect such as silkworm (*Bombyx mori*) or its cells. Further, this invention is concerned with a production process of the cysteine protease gene defective baculovirus and also with a process for the production of an economic protein by using the same.

(ii) Description of the Related Art

In recent years, active research has been conducted with respect to the technology for producing an economic protein with an insect such as silkworm or armyworm (*Autographa carifornia*) or cultured cells thereof by making use of recombinant DNA technology. Among recombinant DNA processes employing these insects or insect cells, those using a baculovirus, especially a nuclear polyhedrosis virus (may hereinafter be abbreviated as "NPV") as a vector are commonly employed (Japanese Patent Application Laid-Open Nos. 9288/1986 and 208276/1987, etc.).

Such recombinant DNA technology, which uses such insects, is considered preferable from the standpoints of the activity, antigenicity and the like of the economic substances to be produced, because such insect cells as hosts are closer genetically to man than *Escherichia coli* and yeast which have been used conventionally. Research is therefore under way on this technology.

Among these recombinant DNA processes, processes making use of living bodies of silkworm, for example, each comprises replacing the polyhedral gene of silkworm nuclear polyhedrosis virus (*Bombyx mori* nuclear polyhedrosis virus; may hereinafter be abbreviated as "BmNPV") with another gene which codes an economic substance, whereby a recombinant virus is created. Silkworm larvae of the fifth instar are inoculated and infected with the recombinant virus. Four to six days later, the economic substance which has been produced by the recombinant virus in silkworm cells and secreted in the body fluid in the course of growth of the recombinant virus is collected, isolated and then purified. These processes are expected to be extremely advantageous from the standpoint of economy because an economic protein can be obtained by simply rearing general silkworms without the need for cell culture and can also be expressed in a large quantity.

It has however come to the surface that, when it is actually attempted to produce an economic protein by inoculating silkworm with a recombinant virus, the quantity of the economic protein increases with the period of rearing until about 5 days after the inoculation but decreases after that, thereby failing to obtain the economic protein as desired.

It has also come to the knowledge that a longer rearing period after inoculation with the recombinant virus results in the production of impurities other than the economic protein in a greater amount, leading to difficult purification and/or a lower yield.

These problems can be satisfactorily explained if one considers that the body fluid of silkworm contains protease which degrades the economic protein. Nothing is however known as to where this protease comes from and about means or the like for inhibiting the action of protease in the living body of silkworm or preventing its formation itself.

SUMMARY OF THE INVENTION

In gene manipulation making use of silkworm of the like, there is hence a long standing demand for the provision of a method for effectively preventing degradation of a once-produced economic protein by protease.

The present inventors proceeded with a variety of research on the protease which is contained in the body fluid of silkworm. As a result, it was found that the protease which decomposes the economic protein is cysteine protease which is different from the acid protease inherently contained in silkworm and having an optimum pH at about pH 2.

Research was also conducted to determine the origin of the protease. The protease was then concluded to have been produced by the recombinant virus which has been employed for the expression of the target gene. A more detailed investigation on the DNA level resulted in the detection of a part in a virus genome, which codes the protease.

Base on the above findings, the present inventors have proceeded with a further investigation. As a result, it has been found that use of a virus whose cysteine protease coding part has been deleted either fully or in part makes it possible to avoid degradation of an economic protein produced in the living bodies of silkworms and also to simplify purification means, leading to the completion of the present invention.

An object of this invention is therefore to provide a gene recombination virus in which at least a part of a cysteine protease gene present on a DNA fragment derived from a nuclear polyhedrosis virus genome has been deleted or substituted by a marker gene.

Another object of the present invention is provide a transfer vector for the production of a cysteine protease defective virus. The transfer vector comprises a DNA fragment of a nuclear polyhedrosis virus genome, in which at least a part of a cysteine protease gene has been substituted by a marker gene, and a plasmid vector fragment.

A further object of the present invention is to provide a process for advantageously producing an economic protein by using the above-described cysteine protease gene defective virus as a parent strain virus for the expression of a foreign (target) gene.

The present invention has been completed based on the finding that there is a protease coding gene, which is different from that originated from silkworm, on a genome of a nuclear polyhedrosis virus as described above and cysteine protease produced by the former protease coding gene degrades an economic protein produced by a recombinant DNA technique.

In one aspect of the present invention, there is thus provided a virus for the expression of a foreign gene, in which at least a part of a cysteine protease gene present on a genome of a baculovirus has been deleted or substituted by a marker gene.

In another aspect of the present invention, there is also provided a transfer vector for the deletion of a cysteine protease gene, which comprises a DNA fragment of a nuclear polyhedrosis virus genome, in which at least a part of a cysteine protease gene has been substituted by a marker gene, and a plasmid vector fragment.

In a further aspect of the present invention, there is also provided a process for the formation of a recombinant virus according to the first aspect of the present invention, which comprises cotransfecting a transfer vector together with the baculovirus genome to insect cells, said transfer vector being formed of a plasmid vector fragment and a genome fragment of the baculovirus whose cysteine protease gene has been substituted at least in part by the marker gene.

In a still further aspect of the present invention, there is also provided a process for the production of an economic protein, which comprises a host insect with a gene recombination virus, said gene recombination virus having been obtained by deleting or substituting by a marker gene at least a part of a cysteine protease gene present on a genome of a baculovirus or a nuclear polyhedrosis virus; expressing an economic protein gene inserted downstream a polyhedral gene promoter, granulin gene promoter or p10 gene promoter of the gene recombination virus; and collecting the economic protein.

When the economic protein is produced using the cysteine protease gene deficient virus strain according to the present invention, degradation of the protein so produced does not take place, thereby permitting efficient production of the protein. The present invention is very useful especially upon production of a protein having high sensitivity to cysteine protease.

Use of the cysteine protease gene deficient virus can suppress not only the degradation of the protein so produced but also breakage of the cell structure of the silkworm, so that the protein can be obtained as a high-purity product without cell-derived impurities, thereby facilitating the purification of the produced protein.

Therefore the present invention can be extremely effectively used upon expression of a useful gene by a recombinant DNA technique which makes use of silkworm. Similar advantageous effects can also be expected with other insects or insect cells.

BRIEF DESCRIPTION OF THE DRAWINGS

The above and other objects, features and advantageous of the present invention will become apparent from the following description and the claims, taken along with the accompanying drawings, in which:

FIG. 3 is an amino acid sequence of a gene coding cysteine protease (SEQ ID NOS: 2-3), as estimated from the restriction map of FIG. 2;

DETAILED DESCRIPTION OF THE INVENTION AND PREFERRED EMBODIMENTS

Figure 1:
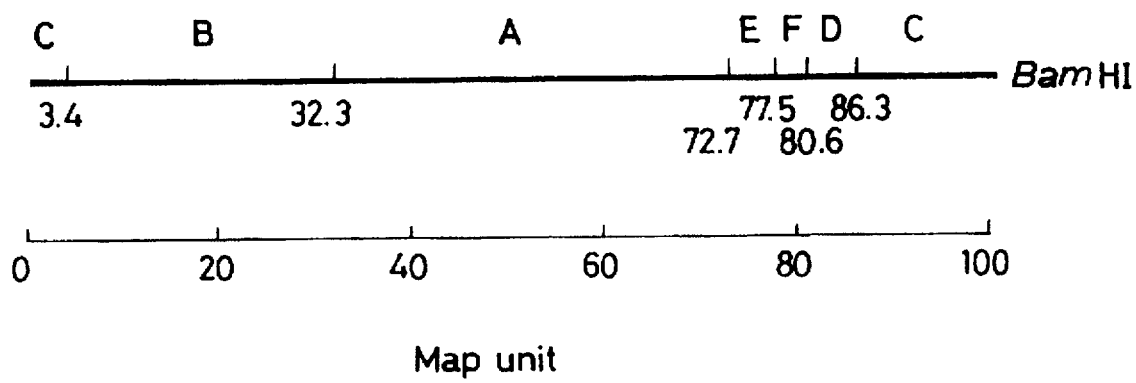
FIG. 1 is a restriction map showing the site of an F fragment, as cleaved by BamHI, on a genome of BmNPV.

The gene which codes cysteine protease was found in the F fragment of 4.2 kb [77.5–80.6 map units; FIG. 1 (Maeda & Majima) 1990] of a virus genome obtained by cleaving the DNA of BMNPV [T3 strain (Maeda et al.) 1985] with BamHI.

Figure 2:
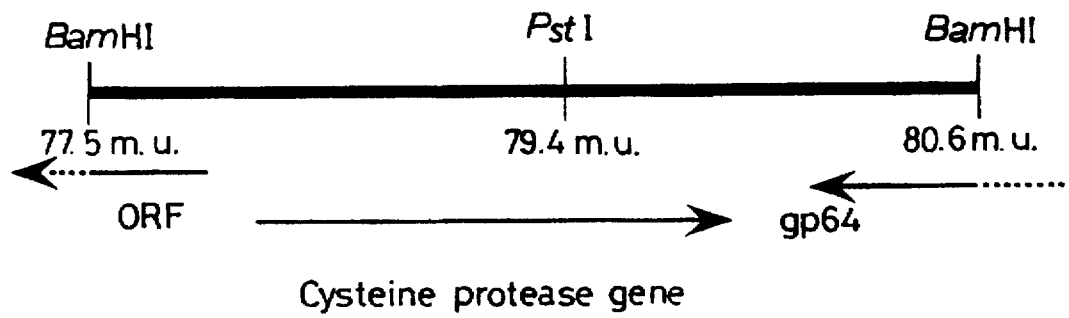
FIG. 2 is a restriction map illustrating the site of cysteine protease on the F fragment of BmNPV.

As a result of determination of the base sequence of the F fragment as cleaved by BamHI, it was found that a portion of the gp64 gene is present on the map of the F fragment of BmNPV as cleaved by BamHI and an open reading frame is present on a left side in the map (FIG. 2). A comparison of its estimated amino acid sequence (FIG. 3) with other amino acid sequences indicated the existence of a high degree of homology with the sequence of papain-like cysteine protease. Although it had the high degree of homology with the sequence of papain-like cysteine protease found on a virus genome of an armyworm NPV (AcNPV) belonging to the same nuclear polyhedrosis viruses [Whitford et al., J. Virol., 63, 1393–1399 (1989)], Rawlings et al. reported that no specific cysteine protease activity was observed on cells inoculated with AcNPV [Rawlings et al., Biol. Chem. Hopper-Seyler, 373, 1211–1215 (1992)].

According to our research, on the other hand, virus-specific cysteine protease was detected from cells inoculated with a nuclear polyhedrosis virus and also from the body fluid of a larva inoculated with the nuclear polyhedrosis virus.

Based on this finding on the cysteine protease gene of BMNPV, a transfer vector for the production of a recombinant virus which does not produce cysteine protease can first be obtained by either deleting a part or the entire part of the cysteine protease gene or substituting a part or the entire part of the cysteine protease gene with a marker gene.

Described specifically, the cysteine protease gene deficient virus can be produced as will be described below.

Using silkworm nuclear polyhedrosis viruses, BmNPV DNA (T3 strain) is first cleaved by BamHI. From fragments thus obtained, F fragments are cloned using a vector plasmid such as pUC19.

The plasmid with the F fragment contained therein is cleaved by a restriction endonuclease appropriately chosen on the basis of the base sequence of the plasmid, whereby a part of the base sequence of the protein of cysteine protease is deleted.

Usable examples of the restriction endonuclease include the combination of ApaI and XcmI. Digestion of the cloning vector with this combination can cut out, as an ApaI-XcmI fragment, a base sequence corresponding to the 114th to 187th amino acids of cysteine protease as counted from the first amino acid thereof.

In this ApaI-XcmI sequence, a sequence is contained around the cysteine residue (the 136th amino acid) forming the active center of cysteine protease. Deletion of at least this sequence should result in elimination of the activity of protease (see FIG. 3).

It is also possible to obtain a transfer vector for the production of a protease gene deficient virus strain (BmNPVCP⁻¹) by deleting a DNA fragment containing a part (or the entire part) of the protein region of cysteine protease, for example, the ApaI-XcmI fragment as described above and then re-joining another fragment of the cloning vector in a manner known per se in the art.

It is however preferred to incorporate a suitable marker gene in place of the thus-deleted cysteine protease gene so that the screening of BmNPVCP⁻ from BmNPV can be facilitated.

Although a known marker gene can be used as the marker gene, the following procedures can be followed, for example, where the β-galactosidase gene is used as the marker gene. Namely, an XbaI-BamHI fragment of pLacZ (Kamita et al., J. Virol. 1993), said fragment containing LacZ and a promoter of hsp 70, is cut out and is then blunt-ended with a Klenow fragment of DNA polymerase I. The resultant product is substituted for the cysteine protease gene, whereby a transfer vector plasmid [pBmFCP(-)LZ] capable of producing β-galactosidase as a marker is obtained.

The thus-obtained transfer vector plasmid according to the present invention is cotransfected together with the DNA of the parent strain virus (BmNPV) into cultured silkworm cells, followed by culturing for an appropriate period so that a cysteine protease gene deficient virus (BmNPVCP⁻) from which the cysteine protease gene has been deleted can be obtained.

As the cultured silkworm cells BmN employed for the proliferation of the virus, it is possible to use, for example, a cell strain which is on deposit as ATCC No. CRL8851 (the American Type Culture Collection).

Further, use of the DNA of the recombinant BmNPV instead of BmNPV makes it possible to directly obtain the cysteine protease gene deficient recombinant virus (BmNPVCP⁻).

Where a marker-producing plaque, for example, pBmFCP(-)is used, these cysteine protease gene deficient BmNPV and recombinant BmNPVCP⁻ can each be readily obtained by screening plaques, which are tinged in a blue color under the action of β-galactosidase, in accordance with a plaque assaying method and then purifying them.

Where a wild-type silkworm nuclear polyhedrosis virus is used, the virus can be produced as will be described hereinafter.

From silkworms (*Bombyx mori*) under rearing, larvae infected with nuclear polyhedrosis virus are collected. The silkworms infected with the nuclear polyhedrosis virus can be easily recognized by inflation of intersegment and oozing white blood from scratches as external pathological symptoms. When the blood is observed under a light microscope, a number of crystalline particles (polyhedra) of 2–4 μm in diameter are found. Many nuclear polyhedrosis viruses are included in these polyhedra.

From the silkworm larvae infected with the nuclear polyhedrosis virus, the body fluid is collected. By centrifuging it at 3,000 rpm for 15 minutes, polyhedra are collected as a precipitate.

These polyhedra are next purified by centrifugation using "Percoll" (trademark; product of Pharmacia AB). Described specifically, a suspension of the body fluid precipitate is piled up on a layer of "Percoll", followed by centrifugation at 25,000 rpm for 30 minutes to isolate a polyhedron layer. Polyhedra thus purified are dissolved with an alkaline solution (0.1M $Na_2CO_3$ and 0.01M NaOH), whereby occluded nuclear polyhedrosis viruses are released. A virus particle layer is then formed by 10–40% sucrose density-gradient centrifugation (15,000 rpm, 30 minutes). Only the virus particle layer is next taken out. The virus particle layer so taken out is centrifuged further at 25,000 rpm for 1 hour, whereby virus particles are collected as a precipitate.

The nuclear polyhedrosis viruses so collected can be stored at −80° C. in the form of a suspension in TE buffer (10 mM Tris-HCl and 1 mM EDTA, pH 8.0). It is only necessary to thaw them before use.

Further, ATCC No. 40188 can also be used as purified DNA of a silkworm nuclear polyhedrosis virus.

To efficiently produce an economic protein by using silkworm in accordance with the present invention, the following procedures can be adopted. Although procedures for deleting a cysteine protease gene from a recombinant virus will be described hereinafter, similar procedures can also be applied to the wild-type virus (BmNPV).

Namely, a transfer plasmid produced as described above, for example, pBmFCP(-)LZ is cotransfected into cultured silkworm cells together with a recombinant BmNPV in which a structural gene portion of the nuclear polyhedron has been substituted by another gene which codes an economic protein. After the cultured silkworm cells so cotransfected are cultured for a predetermined period of time, plaques of the recombinant BmNPVCP⁻ which does not produce cysteine protease are screened. They are inoculated again to cultured silkworm cells. The cultured silkworm cells so inoculated are then cultured and proliferated. Finally, the recombinant BMNPVCP⁻ so proliferated is inoculated to silkworms and is then allowed to proliferate within the silkworms. The economic protein can then be collected from the body fluids of the silkworms.

The above-described production process of the economic protein can be carried out wholly in a manner known per se in the art or in a similar manner except for the use of the recombinant BMNPVCP⁻.

Although the present invention is a technique for preventing production of cysteine protease by entirely or partly deleting the cysteine protease gene on the BmNPV gene, the technique does not affect at all the nuclear polyhedron promoter or the economic protein gene substituted for the subsequent structural gene portion because the cysteine protease gene is located at a site very remote from the portion of the nuclear polyhedral gene on the BmNPV gene.

Accordingly, any of recombinant BmNPVs which have been furnished to date can be used for the production of the recombinant BmNPVCP⁻ according to the present invention. As a result, all economic proteins produced by these recombinant BmNPVs, for example, growth hormones, interferons, AIDS virus envelope glyco-proteins, hepatitis C pellicle protein, luciferase and the like can be advantageously obtained.

Incidentally, acid protease having an optimum pH of 2 or so is inherently contained in the body fluid of silkworm. It has also been revealed that the proteins in the body fluid are not degraded by this protease.

The present invention will hereinafter be described more specifically by the following Examples.

EXAMPLE 1

Detection of Cysteine Protease Gene on Genome of BmNPV

A silkworm nuclear polyhedrosis virus [BmNPV T3 strain; Maeda et al., Nature (1985)] was inoculated to silkworms so that the virus was obtained in a large quantity. Virus particles were purified by sucrose density-gradient centrifugation, treated with proteinase K and 1% SDS and then extracted with phenol, whereby the virus DNA was purified. The purified virus DNA was cleaved by the restriction endonuclease BamHI and separated into fragments A to F by agarose electrophoresis (a physical map of the BmNPV genome is shown in FIG. 1). Of these fragments, the F fragment (77.5–80.6 map units; 3.9 kb; FIG. 2) was purified and then ligated to the BamHI site of the pUC19 vector. The ligation was conducted overnight at 16° C. by using a ligation kit marketed by Takara Shuzo Co., Ltd. A plasmid (pBmFCP) so obtained was transformed into competent cells (*E. coli*, for example, JM109), followed by cloning.

The base sequence of the F fragment was next determined by the dideoxy technique (Sanger et al.) by using a sequencing kit [for example, "SEQUENASE", trademark; product of Toyobo Co., Ltd.]. The sequence was then analyzed.

As a result, the existence of an open reading frame constructed of bases of 973 bp on a left side of the gp64 gene (downstream the gp64 gene) on the map was confirmed. Its amino acid sequence was then estimated to be similar to the sequence of cysteine protease commonly found in general organisms. A base sequence of the open reading frame of cysteine protease is shown together with its estimated amino acid sequence in FIG. 3 (SEQ ID NOS: 2–3.

EXAMPLE 2

Production of Cysteine Protease Gene Deficient Virus

Figure 5:
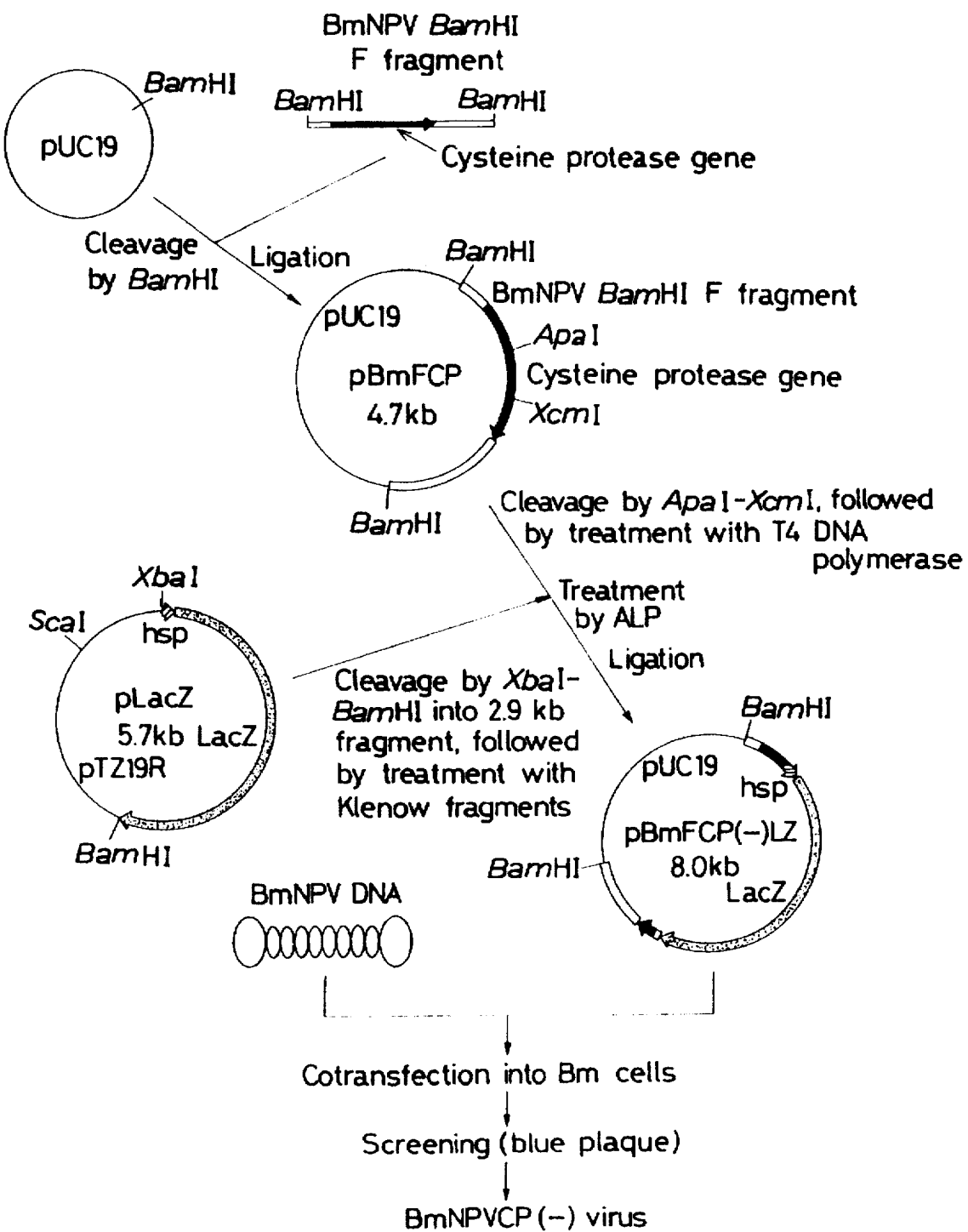
FIG. 5 is a simplified scheme showing procedures for the production of a cysteine protease gene deficient virus.

A virus strain in which the cysteine protease gene in a genome of the virus had been deleted was produced as will be described next (FIG. 5).

(1) A vector plasmid (pBmFCP) which had been obtained by cloning the F fragment of BmNPV was first purified by the alkali technique and then cleaved by the restriction endonucleases ApaI and XcmI.

In the fragment formed by this ApaI-XcmI cleavage, a base sequence corresponding to the sequence of from the 114th amino acid to the 187th amino acid of the cysteine protease sequence as counted from the first amino acid is contained. In this base sequence, is contained a sequence around the cysteine protease residue which forms the active center of cysteine protease.

(2) Next, the pLacZ plasmid (Kamita et al.) was cleaved by XbaI-BamHI so that a β-galactosidase gene cassette accompanied by the hsp promoter of *Drosophila melanogaster* was cut out. The cassette was treated at 37° C. for 30 minutes with the Klenow fragment of DNA polymerase, whereby the cassette was blunt-ended.

On the other hand, the pBmFCP plasmid which had been cleaved by ApaI and XcmI was blunt ended by T4 DNA polymerase (for example, the blunting kit marketed by Takara Shuzo Co., Ltd.) and then dephosphorylated by an alkaline phosphatase (for example, obtained from the calf intestine). To the pBmFCP plasmid so blunted, the blunt ended β-galactosidase gene cassette was inserted and joined. As a consequence, a transfer vector (pBmFCP-LZ) was obtained with the β-galactosidase gene substituted for the sequence of from the 114th amino acid to the 187th amino acid in the cysteine protease gene of the virus. The insertion of the β-galactosidase (marker gene) facilitates screening of a protease gene deficient recombinant virus by the plaque technique.

(3) The pBmFCP-LZ plasmid which had been purified by cesium chloride density-gradient centrifugation was mixed with BmNPV DNA. The resulting mixture was cotransfected by the calcium phosphate technique into Bm cells (BmN cells or BoMol5A 11c cells) which had been cultured at 25° C. in the medium of MGM-448 (added with 10% FBS). The calcium phosphate technique was conducted using "Cellphect Transfection Kit" (trade name; product of Pharmacia AB).

After cultured for 16–20 hours, the medium was replaced by a fresh medium, followed by culturing at 25° C. for 4–5 days to obtain a virus stock.

To screen from the virus stock a virus with the cysteine protease gene deleted (replaced by the β-galactosidase gene), a plaque assay was conducted as will be described next. Namely, an appropriate dilute solution of the virus stock was mixed with BmN cells to inoculate the latter with the former at room temperature. The BmN cells so inoculated were piled up on an agar medium, to which 25 µg/ml of X-gal, a substrate for β-galactosidase, were added. Plaques tinged in a blue color were screened. This plaque purification was repeated further so that a single clone (BmNPVCP⁻) of a recombinant virus from which the cysteine protease gene had been deleted and in which the marker gene incorporated was obtained.

EXAMPLE 3

Characteristics of the Cysteine Protease Gene Deficient Virus

With respect to the cysteine protease gene deficient virus (BmNPVCP⁻) obtained in Example 2, its state of proliferation and the productivity of the cysteine protease were tested.

In the recombinant BmNPV DNA which have been employed in conventional gene manipulation, only the nuclear polyhedral gene portion of the wild-type NPV DNA has been changed to the structural gene of another protein and the portion of the protease gene has been unchanged. A wild-type strain BmNPV capable of forming nuclear polyhedrons (obtained from the National Institute of Sericultural and Entomological Science, the Ministry of Agriculture, Forestry and Fisheries, the Government of Japan) was therefore used in the subsequent tests.

(1) Proliferation

Compared with the wild-type strain BmNPV, no particularly substantial change was observed in the course of proliferation or the like on BMNPVCP⁻. There was hence no significant difference in proliferation therebetween.

The polyhedron-forming ability of BmNPVCP⁻ was also similar to that of the wild-type strain BmNPV, that is, was normal.

(2) Cysteine Protease Activity The activity of protease was measured to test whether the activity of cysteine protease had been eliminated in cultured cells or silkworms which had been inoculated with the cysteine protease gene deficient virus (BmNPVCP⁻). For example, the following two methods can be employed.

According to the first method, "Azocoll" (trademark; product of Sigma Chemical Company) is used as a substrate. The substrate is suspended at a concentration of 3 mg/ml in a buffer (0.1M succinic acid buffer) of pH 4.0 or pH 4.5. A sample is added to the suspension and, while stirring the resultant mixture at 37° C. for several hours, the substrate and the sample are reacted. Two volumes of 10% SDS are added to the reaction system to terminate the reaction. The reaction mixture is centrifuged at 3,000 rpm to collect the supernatant. Its absorbance is then measured at 520 nm.

The other method makes use of a natural substrate. For example, hemoglobin (e.g., product of Merck & Company, Inc.) is employed as a substrate. Acid-denatured hemoglobin is dissolved at a concentration of 1% (w/v) in the above buffer to form a substrate solution. The substrate solution (20 μl) and 60 μl of the (buffer+sample) mixture are combined, followed by reaction at 37° C. for a predetermined time. Then, 80 μl of 10% TCA (trichloroacetic acid) are added to terminate the reaction. The reaction mixture is centrifuged at 10,000 rpm for 5 minutes so that the supernatant is collected. Added to 625 μl of 0.55M $NaCO_3$ are 100 μl of the supernant. The resulting mixture was left over for 5 minutes. Next, 125 μl of 1N phenol reagent are added, followed by incubation at 37° C. for 30 minutes to develop the color. The absorbance is then measured at 660 nm.

BmNPVCP⁻ was inoculated to cultured silkworm cells (either BmN cells or BoMo cells) (about $1\times10^5$ cells). Seventy-two hours after the inoculation, the cells were collected and then treated with a surfactant-containing buffer to solubilize them. The resultant mixture was centrifuged at 15,000 rpm to obtain the supernatant. With respect to the sample, its protease activity was measured. It was found that the activity of protease had dropped markedly compared with the wild-type strain BmNPV. The activity of protease is also recognized at a significant level on non-infected cells (control). This protease activity is however believed attributable to the protease contained in the lysosomes of cells. In the cells inoculated with the wild-type strain virus, the cysteine protease activity derived from the virus is also added on top of the above activity.

By inoculation with a virus, the inherent protease activity of cells tends to decrease. This is supported by the fact that the cells inoculated with BmNPVCP⁻ have lower activity compared with the non-inoculated cells. Further, these activities are almost completely eliminated when E-64, a cysteine protease inhibitor, is added to the reaction mixture. It is hence understood that these proteases can be classified as cysteine proteases.

Figure 4:
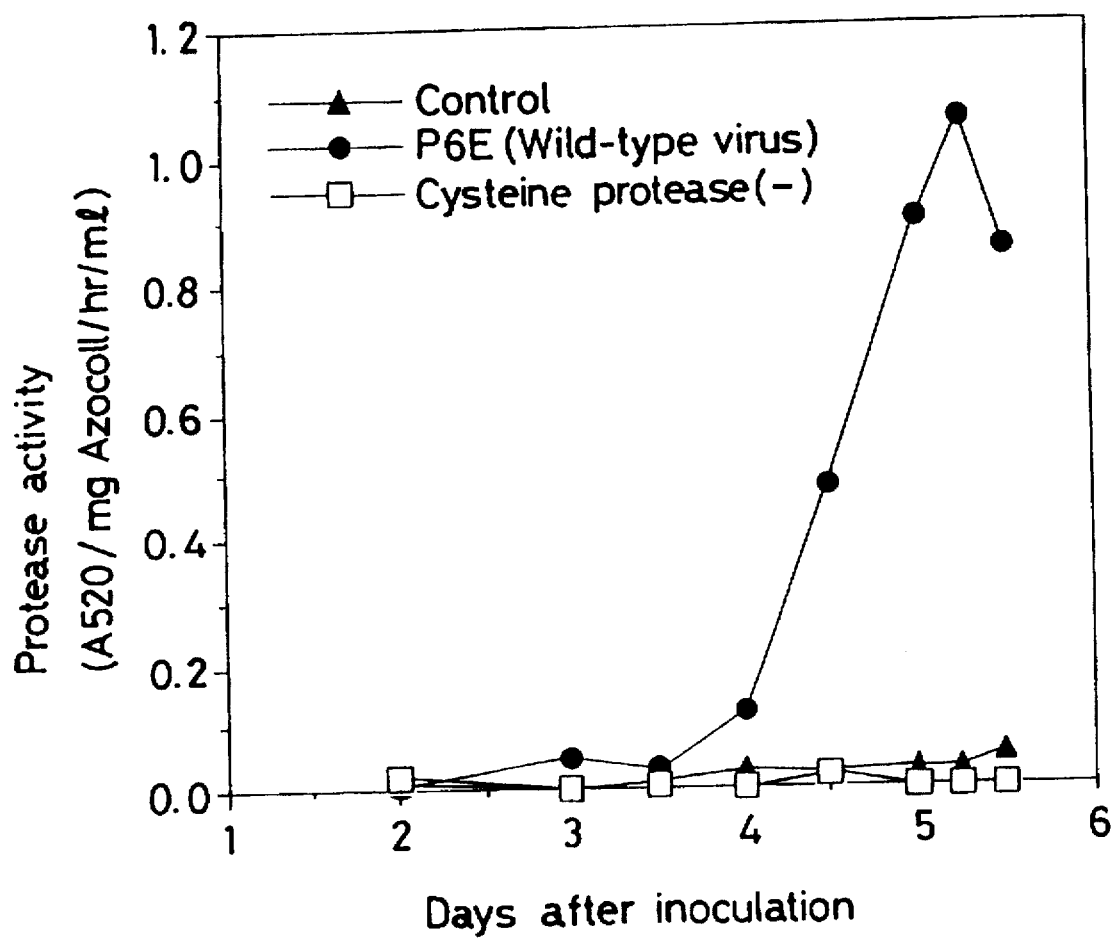
FIG. 4 is a diagram depicting variations in the activity of cysteine protease in the body fluids of silkworms inoculated with wild-type viruses BmNPV and BMNPVCP⁻, respectively.

Further, even when a silkworm larva was inoculated, the activity of cysteine protease in its body fluid never increased throughout an infected period (FIG. 4).

Figure 6A:
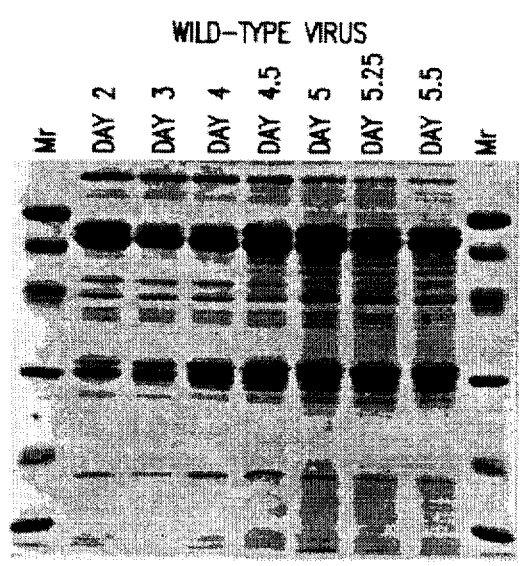
FIG. 6 shows electrophoerograms which illustrate degradation degree of proteins in the body fluids of silkworms inoculated with the wild-type viruses BmNPV and BMNPVCP⁻, respectively.
Figure 6B:
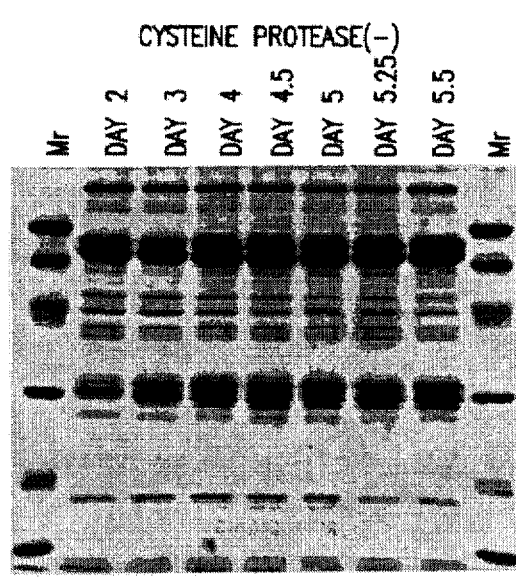

This can be clarified further by analyzing and comparing proteins in the silkworm body fluid in accordance with SDA-PAGE (Laemmli et al.). In silkworm inoculated with the wild-type strain BmNPV, the proteins in its body fluid are progressively degraded as the infection proceeds. In silkworm inoculated with BmNPVCP⁻, however, the proteins in its body fluid were not degraded at all (FIG. 6). Although the body fluid of a silkworm larva contains acid proteases having an optimum pH of 2–3, it is evident from the above results that these acid proteases are irrelevant to the degradation of the proteins of the body fluid but the cysteine protease originated from the virus takes part therein.

When the state of the body fluid of each silkworm was observed, the body fluid of the silkworm inoculated with the wild-type strain BmNPV was found to become more turbid with increasing occurrence of a floating lipid as the infection proceeded. The body fluid of the silkworm inoculated with BmNPVCP⁻ was however observed to remain clear with less occurrence of the lipid.

Figure 7A:
FIG. 7 shows microscopical photographs which illustrate the states of epithelial cells of trachea in silkworms inoculated with the wild-type virus, BmNPV, and BmNPVCP⁻, respectively.
Figure 7B:
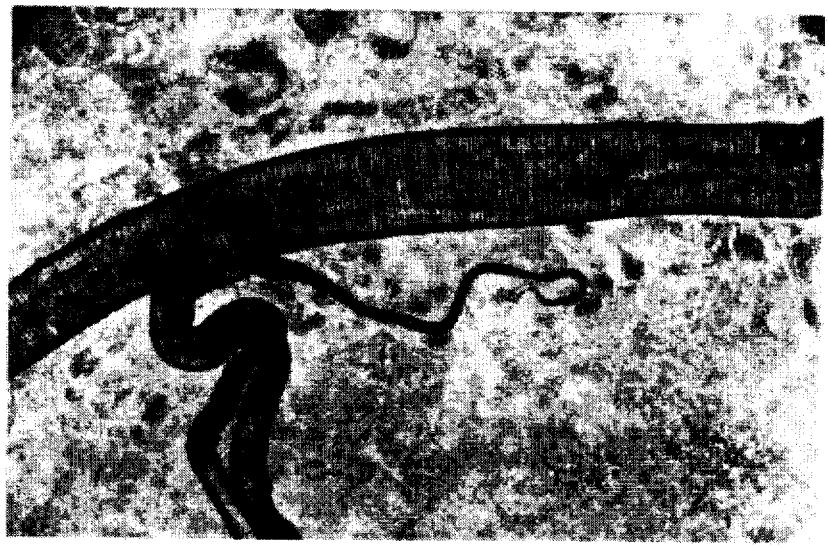

Trancheocapsule cells of the silkworm inoculated with BMNPVCP⁻ were also observed. Capsule cells fully filled with polyhedrons were observed. Cytolysis by infection to the virus was extremely little compared with those of the silkworm inoculated with the wild-type virus (P6E) (FIG. 7).

EXAMPLE 4

Production of Economic Protein

The human growth hormone gene and the firefly luciferase gene were separately recombined to the cysteine protease gene deficient virus (BmNPVCP⁻). Their expressed quantities were compared with the quantities of those expressed by the conventional virus.

(1) Recombinational Procedures

The human growth hormone gene and the firefly luciferase gene were introduced into transfer vector plasmids, respectively. Each plasmid was purified and treated by the alkali technique and cesium chloride density-gradient centrifugation. On the other hand, the BmNPVCP⁻ virus (hereinafter called "the CP⁻ virus") was purified by sucrose density-gradient centrifugation, treated with proteinase K and 1% SDS and then extracted with phenol, whereby the virus DNA was prepared.

The plasmid and the CP⁻ virus DNA so obtained were mixed, and were then cotransfected into Bm cells, which had been cultured at 25° C. as described above, by using calcium phosphate. After cultured for 16–20 hours, the medium was replaced by a fresh medium, followed by further culturing for 4–5 days to obtain a virus stock.

From this virus stock, the virus with the target economic protein gene recombined therein was screened by the limiting dilution analysis. Described specifically, the virus stock was appropriately diluted and then inoculated to Bm cells which had been cultured on a 96-well plate. The Bm cells were cultured at 25° C. for 4–5 days. Polyhedron-free virus was selected under a microscope so that a recombinant was obtained.

(2) Investigation on the Expression of the Human Growth Hormone

First, the conventional wild-type virus with the human growth hormone gene recombined therein (CP⁺hGH) and the CP⁻ virus with the human growth hormone gene recombined therein were separately inoculated to cultured Bm cells. Seventy-two hours later, the cells were collected and proteins were separated by SDS-PAGE. The immunoblotting technique was used for the detection of the protein of the growth hormone. Namely, the protein was electrically transferred from the gel to a nitrocellulose membrane and was then immunologically detected using an antibody (purchased from Hycor Biomedical Inc.) to the human growth hormone. The enzyme-labelled antibody technique was employed for the detection. "ECL Detection Kit" (trade name; product of Amersham Co.) was used.

Figure 8A:
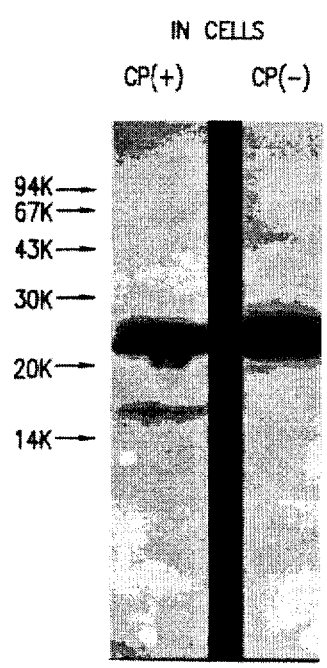
FIG. 8 shows photographs illustrating the results of electrophoretic immunoblotting of the protein of the human growth hormone expressed in the silkworm cells cultured in vitro and in the body fluid of a silkworm larva, respectively.
Figure 8B:
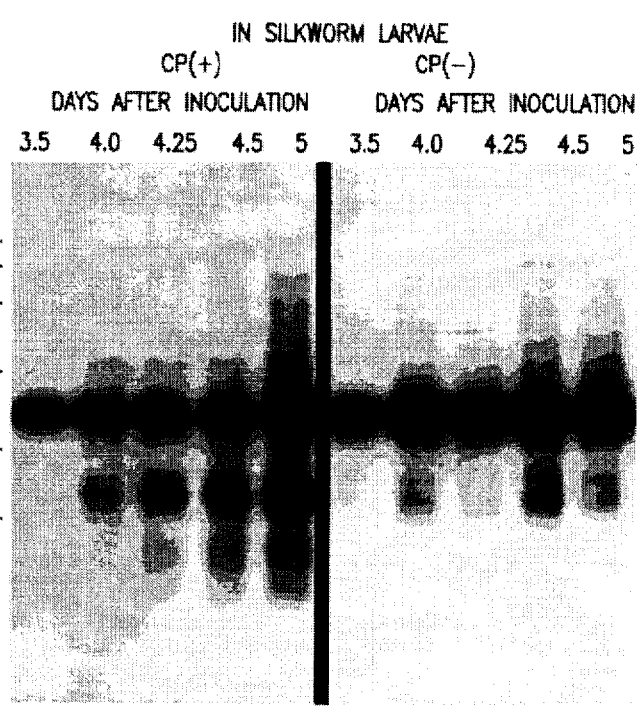

As is shown on the left-hand photograph in FIG. 8, in BmN cell infection, bands of degraded products were observed on a lower molecular weight side than bands (22 kDa and 25 kDa) of the real growth hormone in the case of CP⁺hGH, but such bands were not observed at all in the case of CP⁻hGH.

Likewise, both the viruses were separately inoculated to silkworm larvae of the fifth instar and the human growth hormone in the body fluid of each silkworm larva was detected. In the case of CP⁺hGH, a great deal of degraded products appeared at 16 kDa as the infection proceeded. In the case of CP⁻hGH, on the other hand, degraded products were not observed practically and the human growth hormone of the complete size had been produced (the right-hand photograph in FIG. 8). As is appreciated from the foregoing, it was confirmed that in the case of the CP⁻ virus, degradation which appeared attributable to protease did not occur and the productivity was improved.

(3) Investigation on the Expression of the Firefly Luciferase

The conventional virus (CP⁺PL) and CP⁻ virus (CP⁻PL), in which the firefly luciferase gene had been recombined, were separately inoculated to silkworm larvae of the fifth instar. The luciferase which had accumulated in the body fluid of each silkworm larva was analyzed by the immunoblotting technique.

Figure 9:
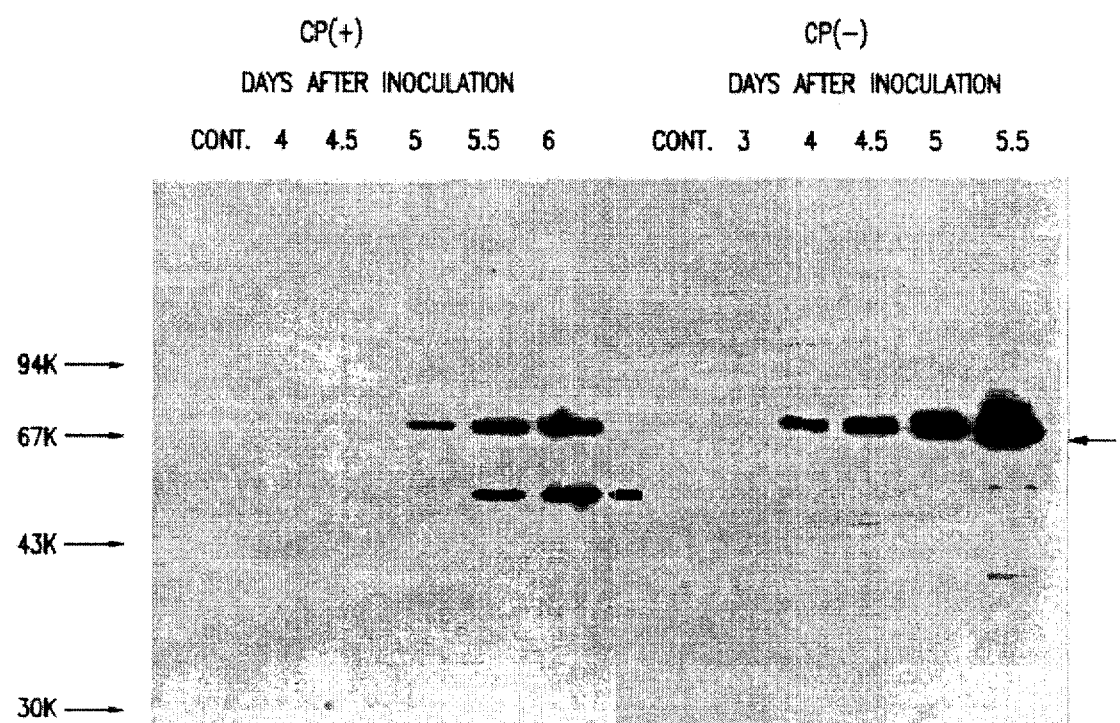
FIG. 9 shows photographs illustrating the results of electrophoretic immunoblotting of firefly luciferase expressed in the body fluid of silkworm larvae.

As a result, as is shown in FIG. 9, a 50 kDa protein band of degraded products of luciferase was observed in addition to a band (66 kDa) of the actual luciferase in the case of CP⁺PL as the infection proceeded, so that degradation was found to proceed. In the case of CP⁻PL, on the other hand, such a band was not observed at all but a band of only the luciferase protein of the complete size was observed, and the quantity of the luciferase protein was 1.5–3 times as much as that available from CP⁺PL. As is understood from the foregoing, it has also become clear that in the production of luciferase, the CP⁻PL virus does not cause degradation of luciferase inside silkworm bodies and considerably improves its productivity.

What is claimed is:

1. A transfer vector for the deletion of a cysteine protease gene, comprising a DNA fragment of a nuclear polyhedrosis virus genome, in which at least a part of a cysteine protease gene has been substituted by a marker gene, and a plasmid vector fragment.

2. A transfer vector according to claim 1, wherein the part of the cysteine protease gene, which has been substituted by the marker gene, is the ApaI-XcmI fragment or ApaI-HpaI fragment of the BamHI-digested DNA F fragment of a silkworm nuclear polyhedrosis virus genome.

3. The transfer vector according to claim 1 wherein the substituent marker gene is a β-galactosidase gene.

4. A nuclear polyhedrosis virus for the expression of a foreign gene, wherein at least a part of the cysteine protease gene present in a genome of said virus has been deleted or substituted by a marker gene.

5. The virus of claim 4, wherein the nuclear polyhedrosis virus is a silkworm nuclear polyhedrosis virus.

6. The virus of claim 4, wherein the substituent marker gene is a β-galactosidase gene.

7. The virus of claim 5, wherein the part of the cysteine protease gene, which has been deleted or substituted by the marker gene is a DNA fragment of a silkworm nuclear polyhedrosis virus genome cloned in a plasmid.

8. The virus of claim 7, wherein the part of the cysteine protease gene, which has been deleted or substituted by the marker gene, is the ApaI-XcmI fragment of the BamHI-digested DNA F fragment of a silkworm nuclear polyhedrosis virus.

9. A process for the formation of a recombinant nuclear polyhedrosis virus, which comprises co-transfecting a transfer vector together with the nuclear polyhedrosis virus genome to insect cells, said transfer vector being formed of a plasmid vector fragment and a genome fragment of a nuclear polyhedrosis virus whose cysteine protease gene has been substituted at least in part by a marker gene and culturing said insect cells so as to produce said recombinant nuclear polyhedrosis virus.

10. A process for the production of an economic protein, which comprises inoculating a host insect with a nuclear polyhedrosis virus having been obtained by deleting or substituting at least a part of a cysteine protease gene present on a genome of a nuclear polyhedrosis virus by a marker gene; expressing an economic protein gene inserted downstream of a polyhedral gene promoter or p10 gene promoter of the nuclear polyhedrosis virus; and collecting the economic protein.

11. The process according to claim 10, wherein said economic protein is selected from the group consisting of growth hormones, interferons, AIDS-virus envelope glycoproteins, hepatitis C pellicle protein and luciferase.

12. The process according to claim 10, wherein said economic protein is a protein which collects in body fluid of silkworms.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
       ( A ) LENGTH: 5883 base pairs
       ( B ) TYPE: nucleic acid
       ( C ) STRANDEDNESS: double
       ( D ) TOPOLOGY: linear ( i i ) MOLECULE TYPE: DNA (genomic)

( v i ) ORIGINAL SOURCE:
       ( A ) ORGANISM: SILKWORM NUCLEAR POLYHEDROSIS VIRUS
       ( B ) STRAIN: BmNPVCP ( i x ) FEATURE:
       ( A ) NAME/KEY: mat_peptide
       ( B ) LOCATION: 1032..4642

( x i ) SEQUENCE DESCRIPTION: SEQ ID NO:1:

| | | | | | | |
|---|---|---|---|---|---|---|
| CCATACGTTC | CAACTGACGT | GAACGTCGAC | TTGTTCTTTG | AGCTTTATTA | AATTTTCGTA | 60 |
| AGCGGTGGCC | TCGTAATTTA | TTTTTACGAG | CGCATAATTG | CGTTCGGCCC | AATCGATCAC | 120 |
| CGGCGTGCCG | GGAATCGCGT | TGGAAACGGC | GACCACCAAC | CACAAAACGT | TTAACAATTT | 180 |
| GTACAACATT | TTAATTTGTC | TTAATTTTAA | GATGTAATTA | TTTTATGTAA | AAAAAAAATG | 240 |
| AACAAAATTT | TGTTTTATTT | GTTTGTGTAC | GCCGTTGTAA | AGAGCGCGGC | CTACGATCCT | 300 |
| TTGAAAGCGC | CTAATTATTT | TGAAGAATTT | GTTCATCGAT | TCAACAAAAA | TTATAGTAGC | 360 |
| GAAGTTGAAA | AATTGCGAAG | ATTCAAAATT | TTCCAACACA | ATTTAAATGA | AATTATCAAT | 420 |
| AAAAACCAAA | ACGATTCGGC | CAAATATGAA | ATAAACAAAT | TCTCGGATTT | GTCCAAAGAC | 480 |
| GAAACTATCG | CAAAATACAC | AGGTCTGTCT | TTGCCTACTC | AGACTCAAAA | TTTTTGCAAG | 540 |
| GTCATACTCT | TAGACCAGCC | GCCGGGTAAA | GGGCCTCTAG | AATCCCAAAA | CAAACCTGGT | 600 |
| TATTGTGGTA | GGTCATTTGT | TTGGCAGAAA | GAAAACTCGA | GAAATTTCTC | TGGCCGTTAT | 660 |
| TCGTTATTCT | CTCTTTTCTT | TTTGGGTCTC | TCCCTCTCTG | CACTAATGCT | CTCTCACTCT | 720 |
| GTCACACAGT | AAACGGCATA | CTGCTCTCGT | TGGTTCCAGA | GAGCGCGCCT | CGAATGTTCG | 780 |
| CGAAAAGAGC | GCCGGAGTAT | AAATAGAGGC | GCTTCGTCTA | CGGAGCGACA | ATTCAATTCA | 840 |
| AACAAGCAAA | GTGAACACGT | CGCTAAGCGA | AAGCTAAGCA | AATAAACAAG | CGCAGCTGAA | 900 |
| CAAGCTAAAC | AATCTGCAGT | AAAGTGCAAG | TTAAAGTGAA | TCAATTAAAA | GTAACCAGCA | 960 |
| ACCAAGTAAA | TAAACTAACA | ACTGCAACTA | CTGAAATCTG | CCAAGAAGTA | ATTATTGAAT | 1020 |
| ACAAGAAGCT | TATGAATCGC | TGGGAAAACA | TTCAGCTCAC | CCACGAAAAC | CGACTTGCGC | 1080 |
| CGCGTGCGTA | CTTTTTTTCA | TATGATTCTG | TTGCGCAAGC | GCGTACCTTT | GCCCGCGAAA | 1140 |
| CCAGCAGCCT | GTTTCTGCCC | TTAAGCGGTC | AGTGGAATTT | CCACTTTTTT | GACCATCCGC | 1200 |
| TGCAAGTACC | AGAAGCCTTC | ACCTCTGAGT | TAATGGCTGA | CTGGGGGCAT | ATTACCGTCC | 1260 |
| CCGCCATGTG | GCAAATGGAA | GGTCACGGCA | AACTGCAATA | TACCGACGAA | GGTTTTCCGT | 1320 |

-continued

| | | | | | |
|---|---|---|---|---|---|
| TCCCCATCGA | TGTGCCGTTT | GTCCCCAGCG | ATAACCCAAC | CGGTGCCTAT | CAACGTATTT | 1380 |
| TCACCCTCAG | CGACGGCTGG | CAGGGTAAAC | AGACGCTGAT | TAAATTTGAC | GGCGTCGAAA | 1440 |
| CCTATTTTGA | AGTCTATGTT | AACGGTCAGT | ATGTGGGTTT | CAGCAAGGGC | AGTCGCCTGA | 1500 |
| CCGCAGAGTT | TGACATCAGC | GCGATGGTTA | AAACCGGCGA | CAACCTGTTG | TGTGTGCGCG | 1560 |
| TGATGCAGTG | GGCGGACTCT | ACCTACGTGG | AAGACCAGGA | TATGTGGTGG | TCAGCGGGGA | 1620 |
| TCTTCCGCGA | TGTTATCTG | GTCGGAAAAC | ACCTAACGCA | TATTAACGAT | TTCACTGTGC | 1680 |
| GTACCGACTT | TGACGAAGCC | TATTGCGATG | CCACGCTTTC | CTGCGAAGTG | GTGCTGGAAA | 1740 |
| ATCTCGCCGC | CTCCCCTGTC | GTCACGACGC | TGGAATATAC | CCTGTTTGAT | GGCGAACGCG | 1800 |
| TGGTGCACAG | CAGCGCCATT | GATCATTTGG | CAATTGAAAA | ACTGACCAGC | GCCACGTTTG | 1860 |
| CTTTTACTGT | CGAACAGCCG | CAGCAATGGT | CAGCAGAATC | CCCTTATCTT | TACCATCTGG | 1920 |
| TCATGACGCT | GAAAGACGCC | AACGGCAACG | TTCTGGAAGT | GGTGCCACAA | CGCGTTGGCT | 1980 |
| TCCGTGATAT | CAAAGTGCGC | GACGGTCTGT | TCTGGATCAA | TAACCGTTAT | GTGATGCTGC | 2040 |
| ACGGCGTCAA | CCGTCACGAC | AACGATCATC | GCAAAGGCCG | CGCCGTTGGA | ATGGATCGCG | 2100 |
| TCGAGAAAGA | TCTCCAGTTG | ATGAAGCAGC | ACAATATCAA | CTCCGTGCGT | ACCGCTCACT | 2160 |
| ACCCGAACGA | TCCGCGTTTT | TACGAACTGT | GTGATATCTA | CGGCCTGTTT | GTGATGGCGG | 2220 |
| AAACCGACGT | CGAATCGCAC | GGCTTTGCTA | ATGTCGGCGA | TATTAGCCGT | ATTACCGACG | 2280 |
| ATCCGCAGTG | GGAAAAAGTC | TACGTCGAGC | GCATTGTTCG | CCATATCCAC | GCGCAGAAAA | 2340 |
| ACCATCCGTC | GATCATCATC | TGGTCGCTGG | GCAATGAATC | CGGCTATGGC | TGTAACATCC | 2400 |
| GCGCGATGTA | CCATGCGGCG | AAACGGCTGG | ATGACACGCG | ACTGGTGCAT | ACGAAGAAG | 2460 |
| ATCGCGATGC | TGAAGTGGTC | GATATTATTT | CCACCATGTA | CACCCGCGTG | CCGCTGATGA | 2520 |
| ATGAGTTTGG | TGAATACCCG | CATCCGAAGC | CGCGCATCAT | CTGTGAATAT | GCTCATGCGA | 2580 |
| TGGGGAACGG | ACCGGGCGGG | CTGACGGAGT | ACCAGAACGT | CTTCTATAAG | CACGATTGCA | 2640 |
| TTCAGGGTCA | TTATGTCTGG | GAGTGGTGCG | ACCACGGGAT | CCAGGCACAG | GACGACCACG | 2700 |
| GCAATGTCTG | GTATAAATTC | GGCGGCGACT | ACGGCGACTA | TCCCAACAAC | TATAACTTCT | 2760 |
| GTCTTGATGG | TTTGATCTAT | TCCGATCAGA | CGCCGGGACC | GGGCCTGAAA | GAGTACAAAC | 2820 |
| AGGTTATCGC | GCCGGTAAAA | ATCCACGCGC | GGGATCTGAC | TCGCGGCGAG | TTGAAAGTCG | 2880 |
| AAAATAAACT | GTGGTTTACC | ACGCTTGATG | ACTACACCCT | GCACGCAGAG | GTGCGCGCCG | 2940 |
| AAGGTGAAAG | CCTCGCGACG | CAGCAGATTA | AACTGCCGGA | CGTTGCGCCG | AACAGCGAAG | 3000 |
| CCCCCTTGCA | GATCACGCTG | CCGCAGCTGG | ACGCCGCGA | AGCGTTCCTC | AACATTACGG | 3060 |
| TGACCAAAGA | TTCCCGCACC | CGCTACAGCG | AAGCCGGACA | CCCTATCGCC | ACTTATCAGT | 3120 |
| TCCCGCTGAA | GGAAAACACC | GCGCAGCCAG | TGCCTTTCGC | ACCAAATAAT | GCGCGTCCGC | 3180 |
| TGACGCTGGA | AGACGATCGT | TTGAGCTGCA | CCGTTCGCGG | CTACAACTTC | GCGATCACCT | 3240 |
| TCTCAAAAAT | GAGTGGCAAA | CCGACATCCT | GGCAGGTGAA | TGGCGAATCG | CTGCTGACTC | 3300 |
| GCGAGCCAAA | GATCAACTTC | TTCAAGCCGA | TGATGATCGA | CAACCACAAG | CAGGAGTACG | 3360 |
| AAGGGCTGTG | GCAACCGAAT | CATTTGCAGA | TCATGCAGGA | ACATCTGCGC | GACTTTGCCG | 3420 |
| TAGAACAGAG | CGATGGTGAA | GTGCTGATCA | TCAGCCGCAC | AGTTATTGCC | CCGCCGGTGT | 3480 |
| TTGACTTCGG | GATGCGCTGC | ACCTACATCT | GGCGCATCGC | TGCCGATGGC | CAGGTTAACG | 3540 |
| TGGCGCTTTC | CGGCGAGCGT | TACGGCGACT | ATCCGCACAT | CATTCCGTGC | ATCGGTTTCA | 3600 |
| CCATGGGAAT | TAACGGCGAA | TACGATCAGG | TGGCGTATTA | CGGTCGTGGA | CCGGGCGAAA | 3660 |
| ACTACGCCGA | CAGCCAGCAG | GCTAACATCA | TCGATATCTG | GCGCCAAGCC | GTCGATGCCA | 3720 |

```
TGTTCGAGAA CTATCCCTTC CCGCAGAACA ACGGTAACCG TCAGCATGTC CGCTGGACGG   3780
CACTGACTAA CCGCCACGGT AACGGTCTGC TGGTGGTTCC GCAGCGCCCA ATTAACTTCA   3840
GCGCCTGGCA CTATACCCAG GAAAACATCC ACGCTGCCCA GCACTGTAAC GAGCTGCAGC   3900
GCAGTGATGA CATCACCCTG AACCTCGATC ACCAGCTGCT TGGCCTCGGC TCCAACTCCT   3960
GGGGCAGCGA GGTGCTGGAC TCCTGGCGCG TCTGGTTCCG TGACTTCAGC TACGGCTTTA   4020
CGTTGCTGCC GGTTTCTGGC GGAGAAGCTA CCGCGCAAAG CCTGGCGTCG TATGAGTTCG   4080
GCGCAGGGTT CTTTTCCACG AATTTGCACA CGGAGAATAA GCAATGAGGA TCATCGATAA   4140
CTTAGAACAG TTCCGCCAGA TTTACGCCTC TGGCAAGAAG TGGCAACGCT GCGTTGAAGC   4200
GATTGAAAAT ATCGACAACA TTCAGCCTGG CGTCGCCCAC TCCATCGGTG ACTCATTGAC   4260
TTACCGCGTG GAGACAGACT CCGCGACCGA TGCGCTATTT ACCGGGCATC GACGCTATTT   4320
TGAAGTGCAT TACTACCTGC AAGGGCAGCA AAAATTGAA TATGCGCCGA AAGAGACATT    4380
ACAGGTAGTG GAATATTATC GTGATGAAAC TGACCGTGAA TATTTAAAAG CTGCGGAGA    4440
AACCGTTGAG GTCCACGAAG GGCAAATCGT TATTTGCGAT ATCCATGAAG CGTATCGGTT   4500
TATCTGCAAT AACGCGGTCA AAAAGTGGT TCTCAAAGTC ACCATCGAAG ATGTTATTTC    4560
CATAACAAAT AACAACTACG GCGGCAAAAG GAGTTTGCCG CCACCGCTAC CCTACTCATT   4620
TTCGGAGATG TGTTATGTCT GAAAAATGGG CGGCGTACAG CTGGAAAGCG ACTATCCATA   4680
CGAAGCAGAC AATAACAATT GCCGTATGAA CTCTAACAAG TTTCTAGTTC AAGTAAAAGA   4740
TTGTTATAGA TACATTATCG TGTACGAGGA AAAACTTAAA GATTGTTAC CCCTTGTCGG    4800
CCCTATTCCT ATGGCCATAG ACGCTGCCGA CATTGTTAAC TATAAACAGG GTATTATAAA   4860
ATATTGTTTC GACAGCGGTC TAAACCATGC GGTTCTTTTA GTGGGTTATG GTGTTGAAAA   4920
CAACATTCCG TATTGGACCT TTAAAAACAC TTGGGGCACG GATTGGGGAG AGGACGGATT   4980
TTTCAGGGTA CAACAAAACA TAAACGCTTG TGGTATGAGA AACGAACTTG CGTCTACTGC   5040
AGTCATTTAT TAATCTCTCG CTATTTGGAA CATAATCATA TCGCCTAAGA TATTTTGTAA   5100
TTAAATATAC AATTAAAAAC TATACAATTT TTTTTATTAC AAATAATGAT ACAATTTTTA   5160
TTATTACATT TAATATTGTC TACTATTACG GTTCTAACC ATACAGTACA AAAATAAAAT    5220
TACAATAAAT ACAATTACAA AAGTGGCTAC ATGACCAAAC ATGAACGAAG TCAATTTGGC   5280
GGCCAATTCG CCTTCAGCCA TGGAAGTGAT GTCGTTCAGA CTGGTGCCGA CGCCGCCAAA   5340
CTTGGTGTTC TCCATGGTGG TTATGAGATT GCTTTTTTGT TGGGCAATAA ACGACCAACC   5400
GCTGGCATCT TTCCAACTGT CGTGATAGGT TGTGTTGCCG ATGGTCGGAA TCCAAAATTC   5460
GACGTCGTCG TCGATTGCTA GTTCCTTGTA GTTGCTAAAA TCTATGCATT GCGACGAGTC   5520
CGTGTTGGCC ACCCAACGCC CTTCTTTGTA AATGCTGTTG TTGTAGCAAT TACTGGTGTG   5580
TGCCGGCGGA TTGGTGCACG GCATCAGCAA AAACGTGTCG TCCGACAAAA ATGTTGAAGA   5640
AACAGAATTG TTCATGAGAT TGCCAATCAA ACGCTCGTCC ACCTTGCCCA CGGAAACTAT   5700
CAGGTCGTGC AGCATATTGT TTATCTTGTT GATATGCGCA TGCATCAGCT CAATGTTCAT   5760
TTTCAGCAAT CGTTTTCGTA CATCAGCTCC TCTTGAATAT GCATCAGGTC GCCTTTGGTG   5820
GCAGTGTCTC CTTCTGTGTA CTTGGCTCTA ACGTTCTGGC GCCAAGTGGG TGGCCGTTTC   5880
TTG                                                                5883
```

( 2 ) INFORMATION FOR SEQ ID NO:2:

( i ) SEQUENCE CHARACTERISTICS:
        ( A ) LENGTH: 972 base pairs
        ( B ) TYPE: nucleic acid 5,753,220

17

18

-continued ( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 1..970

( x i ) SEQUENCE DESCRIPTION: SEQ ID NO:2:

```
ATG AAC AAA ATT TTG TTT TAT TTG TTT GTG TAC GCC GTT GTA AAG AGC        48
Met Asn Lys Ile Leu Phe Tyr Leu Phe Val Tyr Ala Val Val Lys Ser
 1               5                  10                  15

GCG GCC TAC GAT CCT TTG AAA GCG CCT AAT TAT TTT GAA GAA TTT GTT        96
Ala Ala Tyr Asp Pro Leu Lys Ala Pro Asn Tyr Phe Glu Glu Phe Val
             20                  25                  30

CAT CGA TTC AAC AAA AAT TAT AGT AGC GAA GTT GAA AAA TTG CGA AGA       144
His Arg Phe Asn Lys Asn Tyr Ser Ser Glu Val Glu Lys Leu Arg Arg
         35                  40                  45

TTC AAA ATT TTC CAA CAC AAT TTA AAT GAA ATT ATC AAT AAA AAC CAA       192
Phe Lys Ile Phe Gln His Asn Leu Asn Glu Ile Ile Asn Lys Asn Gln
     50                  55                  60

AAC GAT TCG GCC AAA TAT GAA ATA AAC AAA TTC TCG GAT TTG TCC AAA       240
Asn Asp Ser Ala Lys Tyr Glu Ile Asn Lys Phe Ser Asp Leu Ser Lys
 65                  70                  75                  80

GAC GAA ACT ATC GCA AAA TAC ACA GGT CTG TCT TTG CCT ACT CAG ACT       288
Asp Glu Thr Ile Ala Lys Tyr Thr Gly Leu Ser Leu Pro Thr Gln Thr
                 85                  90                  95

CAA AAT TTT TGC AAG GTC ATA CTC TTA GAC CAG CCG CCG GGT AAA GGG       336
Gln Asn Phe Cys Lys Val Ile Leu Leu Asp Gln Pro Pro Gly Lys Gly
            100                 105                 110

CCC CTT GAA TTT GAC TGG CGT CGT CTC AAC AAA GTC ACT AGC GTA AAA       384
Pro Leu Glu Phe Asp Trp Arg Arg Leu Asn Lys Val Thr Ser Val Lys
        115                 120                 125

AAT CAA GGA ATG TGT GGC GCC TGC TGG GCG TTT GCC ACT CTG GGC AGT       432
Asn Gln Gly Met Cys Gly Ala Cys Trp Ala Phe Ala Thr Leu Gly Ser
    130                 135                 140

TTG GAA AGT CAA TTT GCA ATC AAA CAT AAC GAA TTG ATT AAT CTG TCG       480
Leu Glu Ser Gln Phe Ala Ile Lys His Asn Glu Leu Ile Asn Leu Ser
145                 150                 155                 160

GAG CAG CAA ATG ATC GAT TGT GAT TTT GTC GAC GCC GGC TGT AAC GGC       528
Glu Gln Gln Met Ile Asp Cys Asp Phe Val Asp Ala Gly Cys Asn Gly
                165                 170                 175

GGC TTG TTG CAT ACA GCA TTC GAA GCC ATC ATT AAA ATG GGC GGC GTA       576
Gly Leu Leu His Thr Ala Phe Glu Ala Ile Ile Lys Met Gly Gly Val
            180                 185                 190

CAG CTG GAA AGC GAC TAT CCA TAC GAA GCA GAC AAT AAC AAT TGC CGT       624
Gln Leu Glu Ser Asp Tyr Pro Tyr Glu Ala Asp Asn Asn Asn Cys Arg
        195                 200                 205

ATG AAC TCT AAC AAG TTT CTA GTT CAA GTA AAA GAT TGT TAT AGA TAC       672
Met Asn Ser Asn Lys Phe Leu Val Gln Val Lys Asp Cys Tyr Arg Tyr
    210                 215                 220

ATT ATC GTG TAC GAG GAA AAA CTT AAA GAT TTG TTA CCC CTT GTC GGC       720
Ile Ile Val Tyr Glu Glu Lys Leu Lys Asp Leu Leu Pro Leu Val Gly
225                 230                 235                 240

CCT ATT CCT ATG GCC ATA GAC GCT GCC GAC ATT GTT AAC TAT AAA CAG       768
Pro Ile Pro Met Ala Ile Asp Ala Ala Asp Ile Val Asn Tyr Lys Gln
                245                 250                 255

GGT ATT ATA AAA TAT TGT TTC GAC AGC GGT CTA AAC CAT GCG GTT CTT       816
Gly Ile Ile Lys Tyr Cys Phe Asp Ser Gly Leu Asn His Ala Val Leu
            260                 265                 270

TTA GTG GGT TAT GGT GTT GAA AAC AAC ATT CCG TAT TGG ACC TTT AAA       864
```

| Leu | Val | Gly 275 | Tyr | Gly | Val | Glu | Asn 280 | Asn | Ile | Pro | Tyr | Trp 285 | Thr | Phe | Lys | |
|---|---|---|---|---|---|---|---|---|---|---|---|---|---|---|---|---|
| AAC | ACT | TGG | GGC | ACG | GAT | TGG | GGA | GAG | GAC | GGA | TTT | TTC | AGG | GTA | CAA | 912 |
| Asn | Thr 290 | Trp | Gly | Thr | Asp 295 | Trp | Gly | Glu | Asp | Gly 300 | Phe | Phe | Arg | Val | Gln | |
| CAA | AAC | ATA | AAC | GCT | TGT | GGT | ATG | AGA | AAC | GAA | CTT | GCG | TCT | ACT | GCA | 960 |
| Gln 305 | Asn | Ile | Asn | Ala | Cys 310 | Gly | Met | Arg | Asn | Glu 315 | Leu | Ala | Ser | Thr | Ala 320 | |
| GTC | ATT | TAT | T AA | | | | | | | | | | | | | 972 |
| Val | Ile | Tyr | | | | | | | | | | | | | | |

( 2 ) INFORMATION FOR SEQ ID NO:3:

( i ) SEQUENCE CHARACTERISTICS:
        ( A ) LENGTH: 323 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met 1 | Asn | Lys | Ile | Leu 5 | Phe | Tyr | Leu | Phe | Val 10 | Ala | Val | Val | Lys 15 | Ser |
|---|---|---|---|---|---|---|---|---|---|---|---|---|---|---|
| Ala | Ala | Tyr | Asp 20 | Pro | Leu | Lys | Ala 25 | Pro | Asn | Tyr | Phe | Glu 30 | Glu | Phe | Val |
| His | Arg | Phe 35 | Asn | Lys | Asn | Tyr | Ser 40 | Ser | Glu | Val | Glu | Lys 45 | Leu | Arg | Arg |
| Phe | Lys 50 | Ile | Phe | Gln | His | Asn 55 | Leu | Asn | Glu | Ile | Ile 60 | Asn | Lys | Asn | Gln |
| Asn 65 | Asp | Ser | Ala | Lys | Tyr 70 | Glu | Ile | Asn | Lys | Phe 75 | Ser | Asp | Leu | Ser | Lys 80 |
| Asp | Glu | Thr | Ile | Ala 85 | Lys | Tyr | Thr | Gly | Leu 90 | Ser | Leu | Pro | Thr | Gln 95 | Thr |
| Gln | Asn | Phe | Cys 100 | Lys | Val | Ile | Leu | Leu 105 | Asp | Gln | Pro | Pro | Gly 110 | Lys | Gly |
| Pro | Leu | Glu 115 | Phe | Asp | Trp | Arg | Arg 120 | Leu | Asn | Lys | Val | Thr 125 | Ser | Val | Lys |
| Asn | Gln 130 | Gly | Met | Cys | Gly | Ala 135 | Cys | Trp | Ala | Phe | Ala 140 | Thr | Leu | Gly | Ser |
| Leu 145 | Glu | Ser | Gln | Phe | Ala 150 | Ile | Lys | His | Asn | Glu 155 | Leu | Ile | Asn | Leu | Ser 160 |
| Glu | Gln | Gln | Met | Ile 165 | Asp | Cys | Asp | Phe | Val 170 | Asp | Ala | Gly | Cys | Asn 175 | Gly |
| Gly | Leu | Leu | His 180 | Thr | Ala | Phe | Glu | Ala 185 | Ile | Ile | Lys | Met | Gly 190 | Gly | Val |
| Gln | Leu | Glu 195 | Ser | Asp | Tyr | Pro | Tyr 200 | Glu | Ala | Asp | Asn | Asn 205 | Asn | Cys | Arg |
| Met | Asn 210 | Ser | Asn | Lys | Phe | Leu 215 | Val | Gln | Val | Lys | Asp 220 | Cys | Tyr | Arg | Tyr |
| Ile 225 | Ile | Val | Tyr | Glu | Glu 230 | Lys | Leu | Lys | Asp | Leu 235 | Leu | Pro | Leu | Val | Gly 240 |
| Pro | Ile | Pro | Met | Ala 245 | Ile | Asp | Ala | Ala | Asp 250 | Ile | Val | Asn | Tyr | Lys 255 | Gln |
| Gly | Ile | Ile | Lys 260 | Tyr | Cys | Phe | Asp | Ser 265 | Gly | Leu | Asn | His | Ala 270 | Val | Leu |
| Leu | Val | Gly 275 | Tyr | Gly | Val | Glu | Asn 280 | Asn | Ile | Pro | Tyr | Trp 285 | Thr | Phe | Lys |

| | | | | | | | | | | | | | | | |
|---|---|---|---|---|---|---|---|---|---|---|---|---|---|---|---|
| Asn | Thr | Trp | Gly | Thr | Asp | Trp | Gly | Glu | Asp | Gly | Phe | Phe | Arg | Val | Gln |
| | 290 | | | | | 295 | | | | | 300 | | | | |
| Gln | Asn | Ile | Asn | Ala | Cys | Gly | Met | Arg | Asn | Glu | Leu | Ala | Ser | Thr | Ala |
| 305 | | | | | 310 | | | | | 315 | | | | | 320 |
| Val | Ile | Tyr | | | | | | | | | | | | | |